United States Patent
Hessler et al.

(10) Patent No.: US 11,154,405 B2
(45) Date of Patent: Oct. 26, 2021

(54) ARTICULATING EXPANDABLE INTERBODY FUSIONS DEVICES

(71) Applicant: GLOBUS MEDICAL, INC., Audubon, PA (US)

(72) Inventors: Ty Hessler, Phoenixville, PA (US); Chad Glerum, Pennsburg, PA (US); Mark Weiman, Downingtown, PA (US); Albert Hill, Richboro, PA (US); Myles Sullivan, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/750,591

(22) Filed: Jan. 23, 2020

(65) Prior Publication Data

US 2021/0228376 A1 Jul. 29, 2021

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30149* (2013.01); *A61F 2002/4485* (2013.01)

(58) Field of Classification Search
CPC ........ A61F 2/44; A61F 2/4425; A61F 2/4455; A61F 2/447; A61F 2/4611; A61F 2002/4415; A61F 2002/448–4485; A61F 2002/30136–30158; A61F 2002/30535–30545; A61F 2002/30556
See application file for complete search history.

(56) References Cited

U.S. PATENT DOCUMENTS

| | | | |
|---|---|---|---|
| 2019/0008654 A1* | 1/2019 | Thommen | A61F 2/4465 |
| 2019/0231548 A1* | 8/2019 | Ewer | A61F 2/4611 |
| 2020/0345401 A1* | 11/2020 | McHale | A61B 17/8852 |

FOREIGN PATENT DOCUMENTS

WO 2013006669 A2 1/2013

* cited by examiner

*Primary Examiner* — Eduardo C Robert
*Assistant Examiner* — Michelle C Eckman

(57) ABSTRACT

Articulating expandable fusion devices, systems, instruments, and methods thereof. The articulating expandable fusion implant having a plurality of links is capable of being deployed and articulated inside an intervertebral disc space link by link. After the links are articulated into a polygonal shape, the links may be expanded outwardly into an expanded configuration. Instruments may be provided to articulate and expand the implant.

18 Claims, 7 Drawing Sheets

ARTICULATING EXPANDABLE INTERBODY FUSIONS DEVICES

FIELD OF THE INVENTION

The present disclosure relates to surgical devices, and more particularly, to articulating expandable fusion devices capable of being deployed inside an intervertebral disc space and then expanded to maintain disc spacing, restore spinal stability, and/or facilitate an intervertebral fusion.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing conventional fusion devices often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In accordance with the application, devices, systems, methods, and instruments are provided. In particular, an articulating expandable fusion device is provided, which is capable of being deployed inside an intervertebral disc space to maintain normal disc spacing, restore spinal stability, and/or facilitate an intervertebral fusion. The device may be installed in an open, semi-open, or minimally invasive surgical procedure. The articulating expandable fusion device may be capable of being placed into the disc space down a guide tube, for example, articulated into a polygonal shape, and then expanded into an expanded configuration.

According to one embodiment, an expandable implant includes a first link, a second link pivotally connected to the first link, and a third link pivotally connected to the second link. Each of the links comprises an upper body having one or more ramped surfaces, a lower body having one or more ramped surfaces, and a middle body positioned between the upper and lower bodies and having one or more ramped surfaces. Translation of the middle bodies causes the one or more ramped surfaces of the middle bodies to slide against the one or more ramped surfaces of the upper and lower bodies, thereby resulting in expansion of the expandable implant.

The links may be configured to articulate into a polygonal shape, such as a triangle, a square, a pentagon, a hexagon, etc. The one or more ramped surfaces of the upper and lower bodies, respectively, may define male ramps, and the one or more ramped surfaces of the middle bodies may define female ramps or vice versa. One or more of the ramps may mate as dovetail slide ramps, T-slots or similar mechanisms.

The links may be connected by one or more retaining rings configured for holding one or more pivot pins. For example, each of the upper bodies may include first and second upper retaining rings, and each of the lower bodies may include first and second lower retaining rings. The second upper retaining ring of the first link may connect to the first upper retaining ring of the second link with a first pivot pin. The second lower retaining ring of the first link may connect to the first lower retaining ring of the second link with a second pivot pin. The second upper retaining ring of the second link may connect to the first upper retaining ring of the third link with a third pivot pin. The second lower retaining ring of the second link may connect to the first lower retaining ring of the third link with a fourth pivot pin. Additional links, retaining rings, and pivot pins may be used if needed.

According to another embodiment, an implantable device includes a plurality of links configured to articulate with respect to one another. Each of the links may include an upper body, a lower body, and a middle body positioned between the upper and lower bodies. The upper body may include an upper bone contacting surface configured to engage bone and a lower surface having a first ramp. The lower body may include an upper surface having a second ramp and a lower bone contacting surface configured to engage bone. The middle body may include an upper surface having a third ramp and a lower surface having a fourth ramp. The first ramp of the upper body may mate with the third ramp of the middle body and the second ramp of the lower body may mate with the fourth ramp of the middle body. Movement of the middle body may cause the third ramp to slide against the first ramp and the fourth ramp to slide against the second ramp, thereby resulting in an expansion of the upper and lower bodies of the plurality of links.

According to another embodiment, an implantable system includes an articulatable and expandable implant and an inserter instrument. The articulatable and expandable implant may include a plurality of links pivotally connected to one another. Each of the links may include an upper body having one or more ramped surfaces, a lower body having one or more ramped surfaces, and a middle body positioned between the upper and lower bodies and having one or more ramped surfaces configured to mate with the one or more ramped surfaces of the upper and lower bodies, respectively.

The inserter instrument may include a guide tube, an insertion driver, and a cable. The guide tube may be configured for deploying the plurality of links into a disc space. The insertion driver and cable may be configured for articulating the plurality of links into a polygon. The cable may be further configured for applying an inward force to the middle bodies of the links to translate the middle bodies towards a center of the polygon, thereby causing linear expansion of the upper and lower bodies. The middle bodies may include a plurality of openings configured for receiving the cable therein. The insertion driver may apply a push force to the plurality of links and the cable may apply a pull force to the plurality of links to articulate the plurality of links. The cable may be configured to shorten in circumferential distance to provide the inward force against the middle bodies and translate the middle bodies inwards toward the center of the polygon, thereby expanding the implant.

According to yet another embodiment, methods of installing and articulating the expandable implant are provided. A disc space of a patient may be accessed and prepared. The implant may be positioned within the disc space via an inserter instrument, for example, link by link. The links may be articulated by the inserter instrument into a polygon, such as a pentagon. The links may be expanded by moving the middle bodies of the respective links, for example, by translating the middle bodies inward toward the center of the polygon. The inserter instrument may be withdrawn from the patient's body, thereby leaving the implant in the articulated and expanded position.

Also provided are kits including articulating expandable fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Interbody devices have been used to provide support and stability in the anterior column of the spinal vertebrae when treating a variety of spinal conditions, such as degenerative disc disease and spinal stenosis with spondylolisthesis. Clinical treatment of spinal pathologies with anterior vertebral body interbody devices relies on precise placement of the interbody implant to restore normal anterior column alignment. Iatrogenic pathologies may result from the surgical access window to the disc space, failure to precisely place the interbody on hard cortical bone often found on the apophyseal ring of the vertebral body, and/or failure to precisely control and restore normal anatomical spinal alignment.

There currently exists a need to provide precise placement of interbody support that increases interbody contact with hard cortical bone and/or provides precise control of anterior column alignment while reducing the profile of the access window to the disc space. Accordingly, embodiments of the present application are generally directed to devices, systems, instruments, and methods for installing, articulating and expanding the interbody implant. The terms implant, interbody, interbody implant, fusion device, spacer, and expandable device may be used interchangeably herein.

Figure 1:
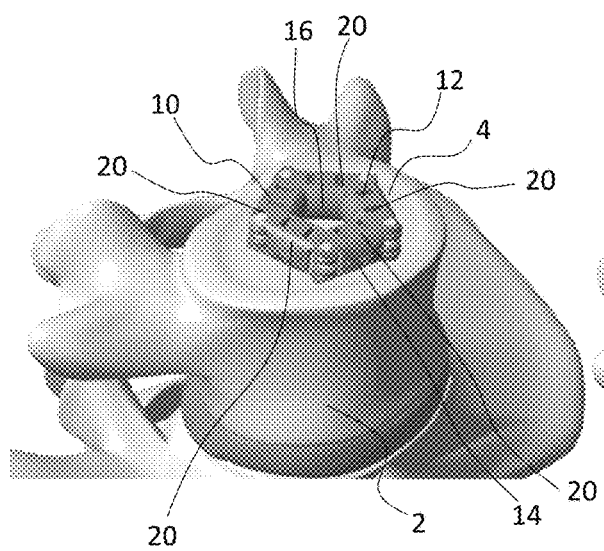
FIG. 1 is a perspective view of an articulating expandable fusion device according to one embodiment, in an articulated collapsed position, shown positioned on a lower vertebra (the upper adjacent vertebra being omitted for clarity)
Figure 2:
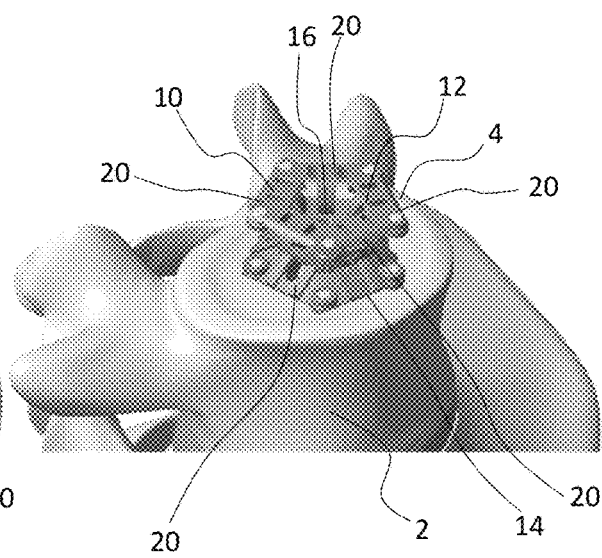
FIG. 2 shows a perspective view of the articulating expandable fusion device of FIG. 1 in an articulated expanded position, shown positioned on the vertebra (the upper adjacent vertebra being omitted for clarity)

Referring now to FIGS. 1 and 2, an articulating expandable fusion device 10 is shown in a disc space between adjacent vertebral bodies 2 (the upper vertebra is omitted for clarity). The fusion device 10 includes a first or upper endplate 12 and a second or lower endplate 14. The upper and lower endplates 12, 14 are configured to engage with the endplates 4 of the adjacent vertebral bodies 2 and, in the installed position, the expanded device 10 is configured to maintain normal intervertebral disc spacing and restore spinal stability, thereby facilitating the intervertebral fusion.

The articulating expandable fusion device 10 may define a central window or opening 16 extending between the upper and lower endplates 12, 14. The central window or opening 16 may be configured to receive bone graft or a similar bone growth inducing material. The bone graft can be introduced within and/or around the fusion device 10 to further promote and facilitate the intervertebral fusion. The fusion device 10, in one embodiment, is preferably packed with bone graft or similar bone growth inducing material to promote the growth of bone through and around the fusion device 10. Such bone graft may be packed between the endplates 4 of the adjacent vertebral bodies 2 prior to, subsequent to, or during implantation of the fusion device 10.

In FIG. 1, the fusion device 10 is shown in an articulated position with the device 10 in a collapsed or contracted position, such that the distance between the upper and lower endplates 12, 14 is provided at a first height. In FIG. 2, the fusion device 10 is shown in an articulated position with the device 10 in an expanded position, such that the distance between the upper and lower endplates 12, 14 is provided at a second height, greater than the first height. The articulating expandable fusion device 10 can be manufactured from a number of biocompatible materials including, but not limited to, titanium, stainless steel, titanium alloys, non-titanium metallic alloys, polymeric materials, plastics, plastic composites, PEEK, ceramic, and elastic materials.

With further emphasis on FIGS. 1-4, the articulating expandable fusion device 10 includes a plurality of individual linking segments or links 20. The plurality of linking segments or links 20 are configured to articulate into a generally polygonal shape. The polygon may be convex, concave, simple, intersecting, or of other suitable type. The shape of the polygon may be dictated by the number of segments or links 20 used to build the implant 10. For example, a device 10 with three links 20 may form a triangle, four links 20 may form a quadrilateral, five links 20 may form a pentagon, six links 20 may form a hexagon, etc. Although the device 10 is shown with five links 20 forming a generally pentagonal shape, it is envisioned that the device 10 may have as few as three segments 20 or as many as desired. The polygon may be equilateral with all links 20 having the same length or the links 20 may be of different lengths. The polygon may be equiangular with all angles between links 20 being equal or may be of different angles and forming irregular shapes.

Figure 3:
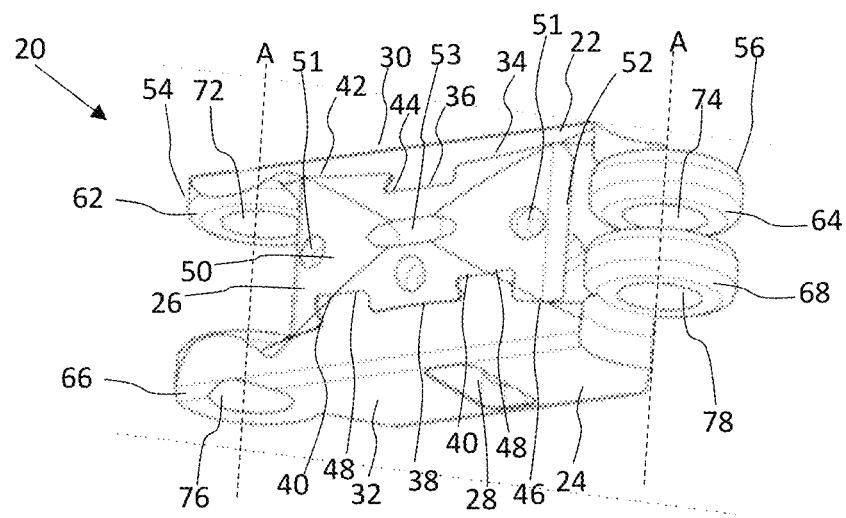
FIG. 3 shows a perspective view of a single link from the articulating expandable fusion device of FIG. 1, with the link in a collapsed position.
Figure 4:
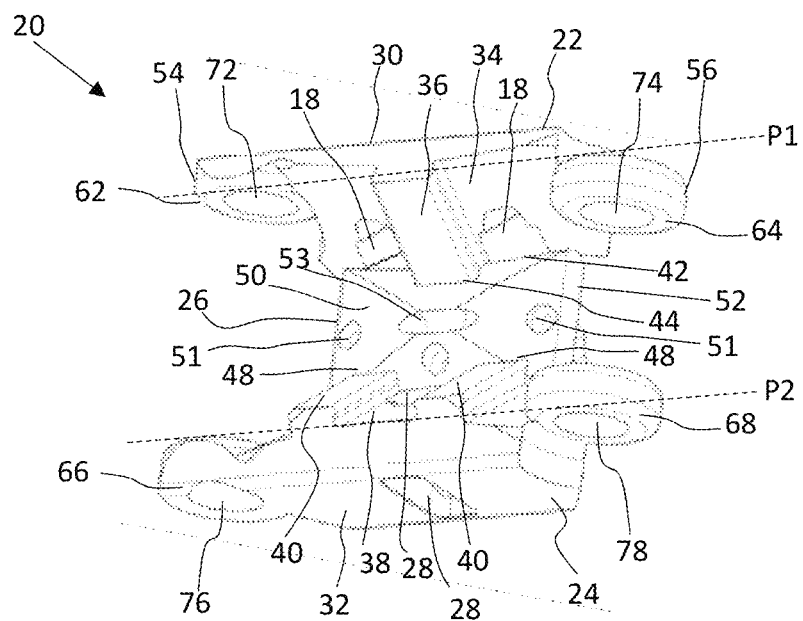
FIG. 4 shows a perspective view of the single link of FIG. 3 with the link in an expanded position.

With further reference to FIGS. 3 and 4, a single link 20 of the device 10 is shown in greater detail. In the embodiment shown, it will be understood that all of the links 20 are identical. It is envisioned, however, that the links 20 may be different from one another. The single link 20 is shown in FIG. 3 in a collapsed or contracted position, and in FIG. 4 in an expanded position. Each link 20 comprises a first body or upper body 22, a second body or lower body 24, and a third inner body or middle body 26 positioned between the upper and lower bodies 22, 24. The upper body 22 includes a bone contacting surface or upper surface 30 which forms a portion of the upper endplate 12 of the device 10 and is configured to engage the endplate 4 of the upper vertebral body 2 (not shown). The lower body 24 includes a bone contacting surface or lower surface 32 which forms a portion of the lower endplate 14 of the device 10 and is configured to engage the endplate 4 of the lower vertebral body 2 (shown in FIGS. 1 and 2).

Figure 5:
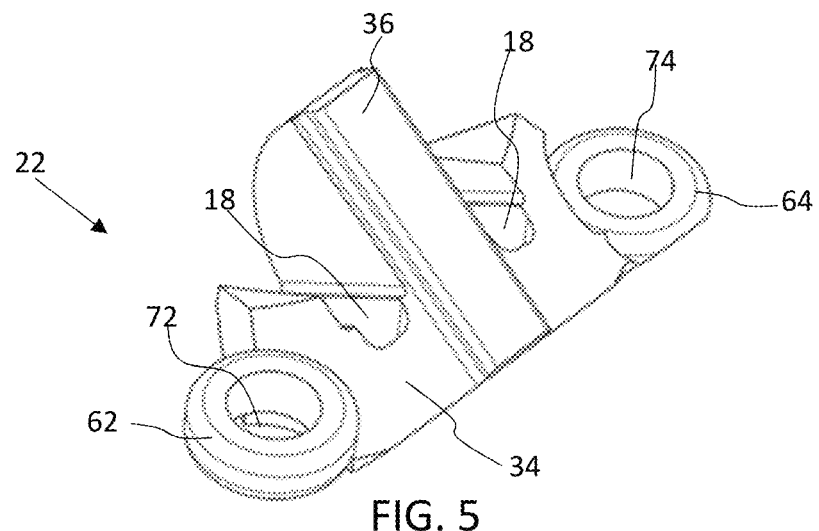
FIG. 5 is a perspective view of the upper body of the link shown in FIGS. 3 and 4.
Figure 6:
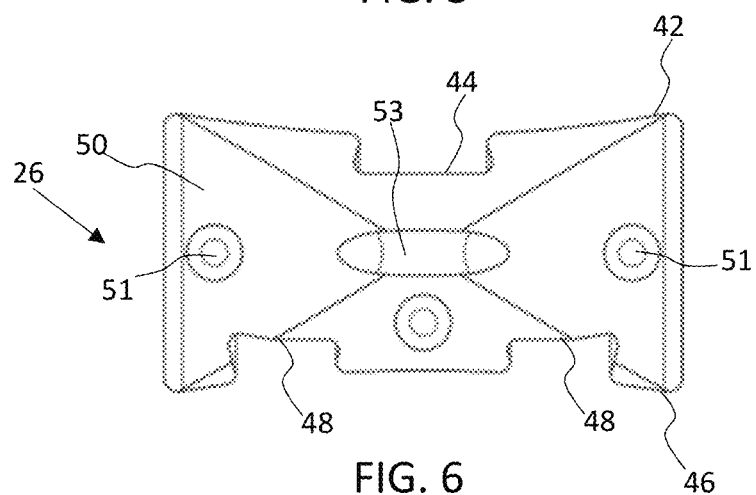
FIG. 6 is a side view of the middle body of the link shown in FIGS. 3 and 4.
Figure 7:
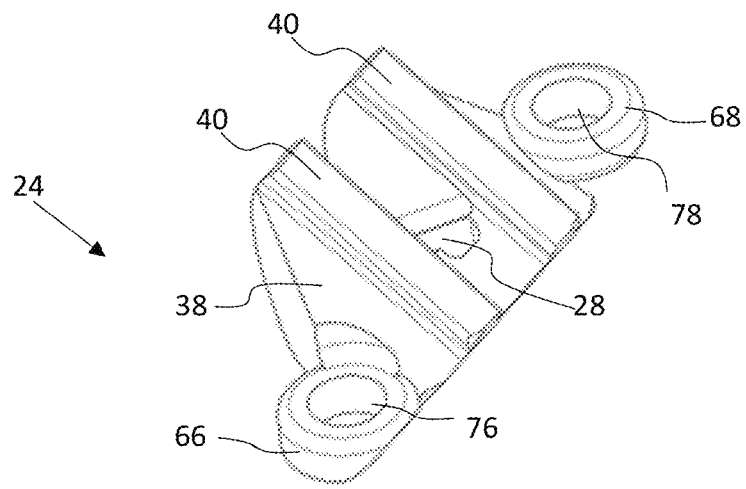
FIG. 7 is a perspective view of the lower body of the link shown in FIGS. 3 and 4.

As best seen in FIG. 5, the upper body 22 includes a lower surface 34 having one or more ramped surfaces 36. The ramped surface 36 may be an angled continuous surface with a given angle of slope. The ramped surface 36 may include male slide ramps or protruding ramps. In the embodiment shown in FIG. 5, a single ramped surface 36 is protruding from the lower surface 34 of the upper body 22. The single ramp 36 may be generally located at the center or midline of the upper body 22. As best seen in FIG. 7, the lower body 24 also includes an upper surface 38 having one or more ramped surfaces 40. The ramped surfaces 38 may be angled continuous surfaces with the same given angle of slope. The ramped surfaces 40 may include male slide ramps or protruding ramps. In the embodiment shown in FIG. 7, two ramped surfaces 40 are protruding from the upper surface 38 of the lower body 24. The two ramped surfaces 40 may be spaced apart at an equal distance such that the ramps 40 are substantially parallel to one another. Although a specific arrangement of ramped surfaces 36, 40 is shown, it is envisioned that the number, location, and configuration of ramped surfaces 36, 40 may be modified or selected by one skilled in the art.

The upper body 22 may include one or more openings 18 extending from the lower surface 34 to the upper surface 30 or recessed through a portion thereof. The openings 18 may be configured to receive a portion of the ramps 40 of the lower body 24, for example, when the links 20 are in the collapsed position. Similarly, the lower body 24 may include one or more openings 28 extending from the upper surface 38 to the lower surface 24 or recessed through a portion thereof. The opening 28 may be configured to receive a portion of the ramp 36 of the upper body 22, for example, when the links 20 are in the collapsed position. In addition, the openings 18, 28 may be configured to receive graft material, if desired.

The male ramped surfaces 36, 40 are configured to mate with corresponding female ramped surfaces 44, 48 in the middle body 26. The middle body 26 may include an upper surface 42 having one or more female ramped surfaces 44 recessed into the upper surface 42 and a lower surface 46 having one or more female ramped surfaces 48 recessed into the lower surface 46. The protruding male ramped surface 36 of the upper body 22 may be configured to be received within the recessed female ramped surface 44 of the middle body 26 and the protruding male ramped surfaces 40 of the lower body 24 may be configured to be received within the recessed female ramped surfaces 48 of the middle body 26. The ramped surfaces 44, 48 may be angled continuous surfaces with given angles of slope. The angle of slope of the female ramps 44, 48 may match the angle of slope of their respective male ramps 36, 40. Although the ramps 36, 40 are shown as male ramps and the ramps 44, 48 are shown as female ramps, it is envisioned that these ramps could be reversed such that the upper and lower bodies 22, 24 have the female portions and the middle body 26 includes the male portions.

The male ramped surfaces 36, 40 and female ramped surfaces 44, 48 may be configured to mate such that a slidable dovetail joint is formed. For example, a slidable dovetail joint may be formed by one or more tapered projections or tenons (ramps 36, 44) which interlock with corresponding tapered recesses or mortises (ramps 44, 48). The protrusions of the male ramps 36, 40 may be tapered such that they are narrower towards the base and wider towards the mating surfaces of the female ramps 44, 48. Similarly, the recesses of the female ramps 44, 48 may be tapered such that they are narrow towards surfaces 42, 46 and wider toward the mating surfaces of the male ramps 36, 40. The male ramped surface 36, 40 and female ramped surfaces 44, 48 may be substantially linear along their lengths or may be curved, stepped, or otherwise configured to provide for the desired type and amount of expansion between the upper and lower bodies 22, 24.

The inner or middle body 26 includes an outer surface 50 and an inner surface 52. The outer surface 50 is configured to face outwardly when the plurality of links 20 are articulated into the polygonal shape. The inner surface 52 is configured to face inwardly when the plurality of links 20 are articulated into the polygonal shape. The inner surfaces 52 of the links 20 may partially define the central opening 16 of the device 10 when in the expanded position. One or more openings 51, 53 may be provided along or through the outer surface 50 of the middle body 26. For example, a plurality of openings 51 may extend through the outer surface 50 of the middle body 26 and may be configured to receive a wire or cable 76 of an inserter device 70. The face of the outer surface 50 may also define a recess 53. The recess 53 may be elongated having a length greater than its width and configured to receive a portion of the cable 76 of the inserter device 70. The openings 51 and recess 53 may be aligned along a common axis. The recess 53 may be configured to guide the cable 76 between the two openings 51 on either side of the recess 53. Operation of the cable 76 and inserter device 70 will be described in more detail below.

With further emphasis on FIGS. 3 and 4, the expansion mechanism will be further described. In the collapsed or contracted position shown in FIGS. 1 and 3, the middle body 26 is generally positioned towards the perimeter or outer wall of the implant 10 and the upper and lower surfaces 30, 32 are provided at their smallest, initial height. When all of the links 20 are collapsed, the upper and lower endplates 12, 14 of the implant 10 are collapsed (FIG. 1). As an inward force is provided against each of the middle bodies 26, the force translates the middle body 26 inwards toward the center of the polygon, resulting in linear expansion of the upper and lower surfaces 30, 32 of the upper and lower bodies 22, 24.

As shown in the expanded position in FIGS. 2 and 4, the middle body 26 is generally positioned towards the inside or center of the implant 10 and the upper and lower surfaces 30, 32 are provided at their greatest, expanded height. Thus, movement of middle body 26 along the respective ramps 36, 40 of the upper and lower bodies 22, 24 toward the inside or center of the device 10 causes the upper and lower bodies 22, 24 to expand away from one another. When all of the links 20 are expanded, the upper and lower endplates 12, 14 of the implant 10 are expanded (FIG. 2). Similarly, if the middle body 26 was moved along the ramps 36, 40 in the opposite direction toward the outside of the device 10, the upper and lower bodies 22, 24 collapse toward one another, thereby returning to the collapsed position.

Figure 8:
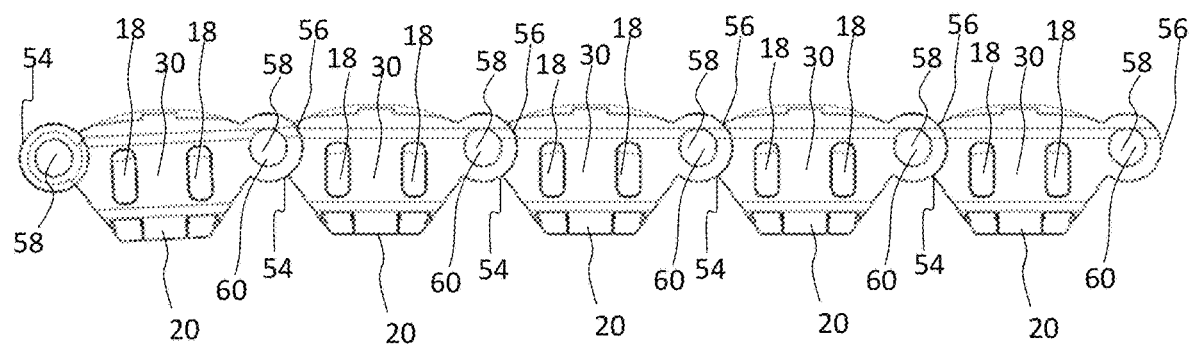
FIG. 8 shows a top view of the articulating expandable fusion device of FIG. 1 with a plurality of links aligned in a substantially straight or non-articulated position.

Turning now to FIG. 8, a plurality of links 20 in a generally linear configuration is shown. Each link 20 extends from a first end 54 to a second end 56. In the embodiment shown, five links 20 are connected such that the second end 56 of a given link 20 connects to the first end 54 of the next link 20 in the chain. For example, the second end 56 of the first link 20 connects to the first end 54 of the second link 20, the second end 56 of the second link 20 connects to the first end 54 of the third link 20, the second end 56 of the third link 20 connects to the first end 54 of the fourth link 20, the second end 56 of the fourth link 20 connects to the first end 54 of the fifth link 20. The linkages would continue if further links 20 were provided. Once articulated into the final polygonal shape, the second end 56 of the fifth link 20 connects to the first end 54 of the first link 20.

Each of the links 20 are connected and able to articulate about a joint 58. The joint 58 may be a revolute joint such as a pin joint or hinge joint. For example, the joint 58 may provide a uni-axial rotation or single-axis rotation about one or more pins 60, for example. The connected links 20 may be able to rotate freely about the axis A of each respective pin 60 between connected links 20. Although pins 60 are exemplified herein, it will be appreciated that other joint geometries may be used.

In one embodiment, the joints 58 may include a plurality of retaining rings 62, 64, 66, 68. As best seen in FIGS. 3 and 4, each upper body 22 may include first and second upper retaining rings 62, 64, and each lower body 24 may include first and second lower retaining rings 66, 68. For example, the upper body 22 may include first upper retaining ring 62 at the first end 54 and second upper retaining ring 64 at the second end 56 of the link 20. The lower body 24 may include first lower retaining ring 66 at the first end 54 and second lower retaining ring 68 at the second end 56 of the link 20. The first upper retaining ring 62 may be generally aligned with the first lower retaining ring 66 and the second upper retaining ring 64 may be generally aligned with the second lower retaining ring 68. The retaining rings 62, 64, 66, 68 may define a generally circular or rounded outer body or may be otherwise configured to provide movement of the joints 58. The retaining rings 62, 64, 66, 68 may define cylinders, tubes, polyhedrons, prisms, or other suitable shapes.

As best seen in FIG. 4, the first rings 62, 66 may be generally offset relative to the second rings 64, 68. For example, the first upper ring 62 may be generally positioned above a first plane P1 whereas the second upper ring 64 may be generally positioned below the first plane P1. The first lower ring 66 may be generally positioned below a second plane P2 and the second lower ring 68 may be generally positioned above the second plane P2. In this configuration, regardless of the amount of expansion, the distance between the first upper ring 62 and the first lower ring 66 is greater than the distance between the second upper ring 64 and the second lower ring 68. In addition, in the embodiment shown, the first upper retaining ring 62 may have at least a portion of its upper surface generally aligned with the bone contacting surface 30 of the upper body 22 and the first lower retaining ring 66 may have at least a portion of its lower surface generally aligned with the bone contacting surface 32 of the lower body 24. Although the offsets are shown in a given configuration, it will be appreciated that the number, location, and type of retaining rings may be modified.

The retaining rings 62, 64, 66, 68 define respective openings 72, 74, 76, 78 extending therethrough configured to receive one or more pivot pins 60. For example, ring 62 may include a central opening 72 extending from an upper surface to a lower surface of the ring 62. Ring 64 may include a central opening 74 extending from an upper surface to a lower surface of the ring 64. Ring 76 may include a central opening 76 extending from an upper surface to a lower surface of the ring 66. Ring 68 may include a central opening 78 extending from an upper surface to a lower surface of ring 68. Openings 72 and 76 may be generally aligned and openings 74 and 78 may be generally aligned with one another.

By way of example, mating of the retaining rings 62, 64, 66, 68 between links 20 will be described with respect to a series of three links 20. Although it will be appreciated that such connections (including additional retaining rings 62, 64, 66, 68 and pivot pins 60) may continue in series when additional links 20 are present. The second upper retaining ring 64 of the first link 20 connects to the first upper retaining ring 62 of the second link 20 with a first pivot pin 60. The second lower retaining ring 68 of the first link 20 connects to the first lower retaining ring 66 of the second link 20 with a second pivot pin 60. The second upper retaining ring 64 of the second link 20 connects to the first upper retaining ring 62 of the third link 22 with a third pivot pin 60. The second lower retaining ring 68 of the second link 20 connects to the first lower retaining ring 66 of the third link 20 with a fourth pivot pin 60.

Figure 9:
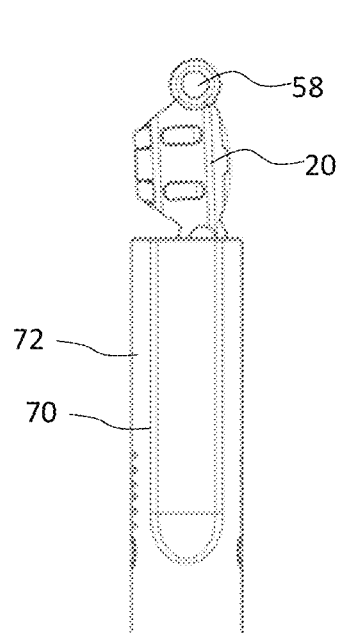
FIG. 9 shows a top view of the articulating expandable fusion device of FIG. 1 with a first link deployed through an inserter instrument according to one embodiment.
Figure 10:
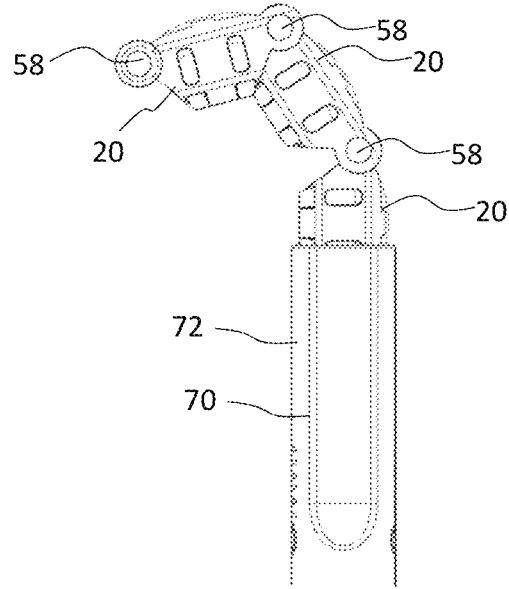
FIG. 10 shows a top view of the articulating expandable fusion device of FIG. 1 with a plurality of links deployed through the inserter instrument and beginning to articulate.
Figure 11:
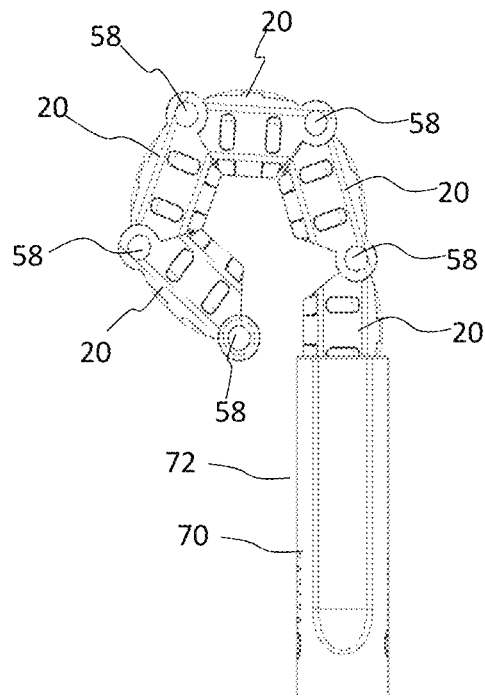
FIG. 11 shows a top view of the articulating expandable fusion device of FIG. 1 with a plurality of links deployed through the inserter instrument and almost fully articulated into a polygonal shape.
Figure 12:
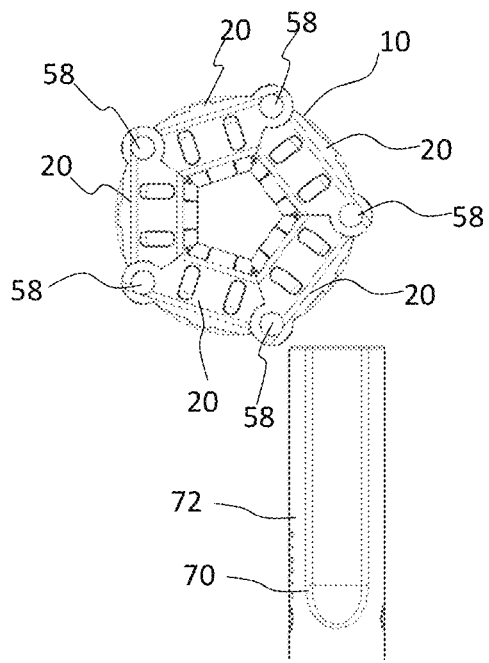
FIG. 12 is a top view of the articulating expandable fusion device of FIG. 1 completely deployed from the inserter instrument and fully articulated in a collapsed position.

FIG. 8 depicts the plurality of links 20 in a generally linear configuration suitable for being guided through an inserter instrument 70. FIGS. 9-12 depicts deployment of the links 20 through the inserter instrument 70 in a collapsed position. The inserter instrument 70 may include a cannula or guide tube 72 that the links 20 can pass through. The guide tube 72 may be suitable for use during a minimally invasive surgical (MIS) procedure, for example. As shown in FIG. 9, a first link 20 is deployed through the inserter instrument 70 in a collapsed position. In FIG. 10, additional links 20 are deployed through the inserter instrument 70 and the links 20 are beginning to articulate. In FIG. 11, most of the links 20 are deployed through the inserter instrument 20 and the links 20 are almost fully articulated into its polygonal shape (a pentagon in this case). In FIG. 12, the implant 10 is completely deployed from the inserter instrument 70 and all of the links 20 are fully articulated into a polygon in the collapsed position.

Figure 13:
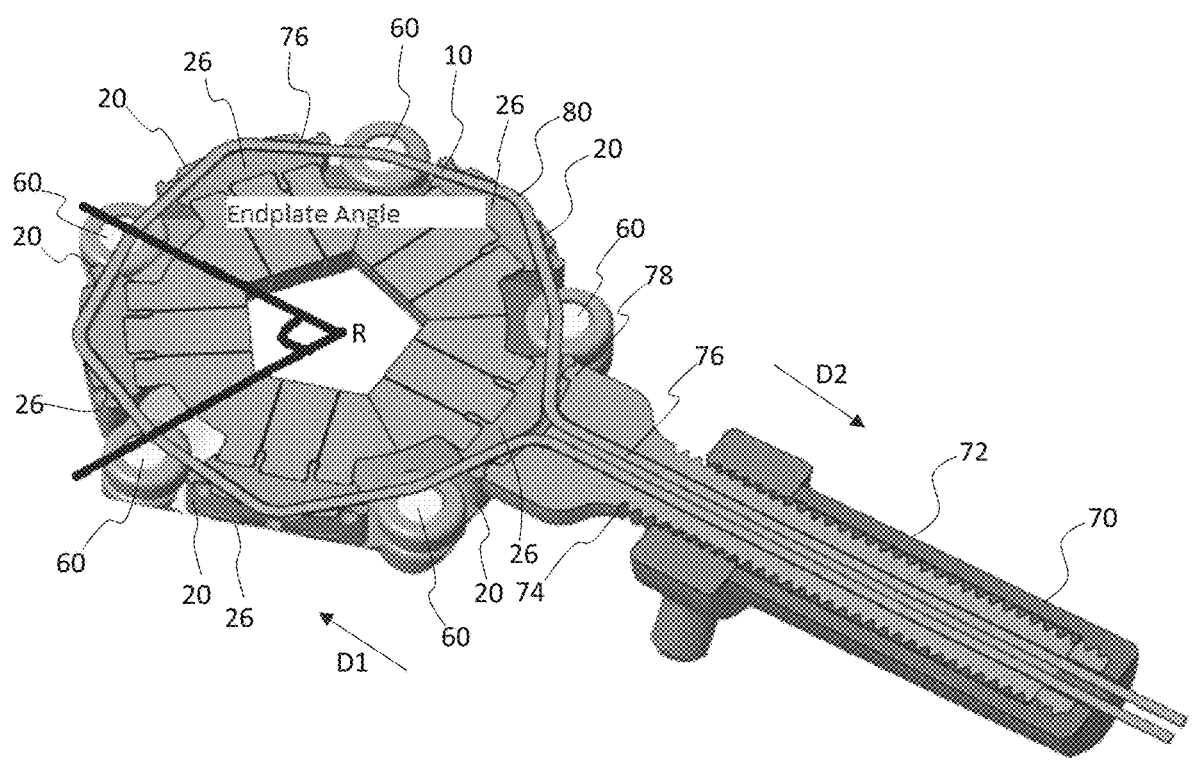
FIG. 13 is a cross-sectional view of the articulating expandable fusion device in the collapsed position and an instrument configured for expanding the fusion device.

Although five links 20 are depicted in this embodiment to form a pentagon, it will be appreciated that a suitable number of links 20 may be selected. As best seen in FIG. 13, a reference angle R of the endplates of the assembled links 20 is dictated by the number of links 20 used to build the implant 10. For example, the reference angle R for a triangle is 120 degrees, reference angle R for a square is 90 degrees, reference angle R for a pentagon is 72 degrees, reference angle R for a hexagon is 60 degrees, etc.

Figure 14:
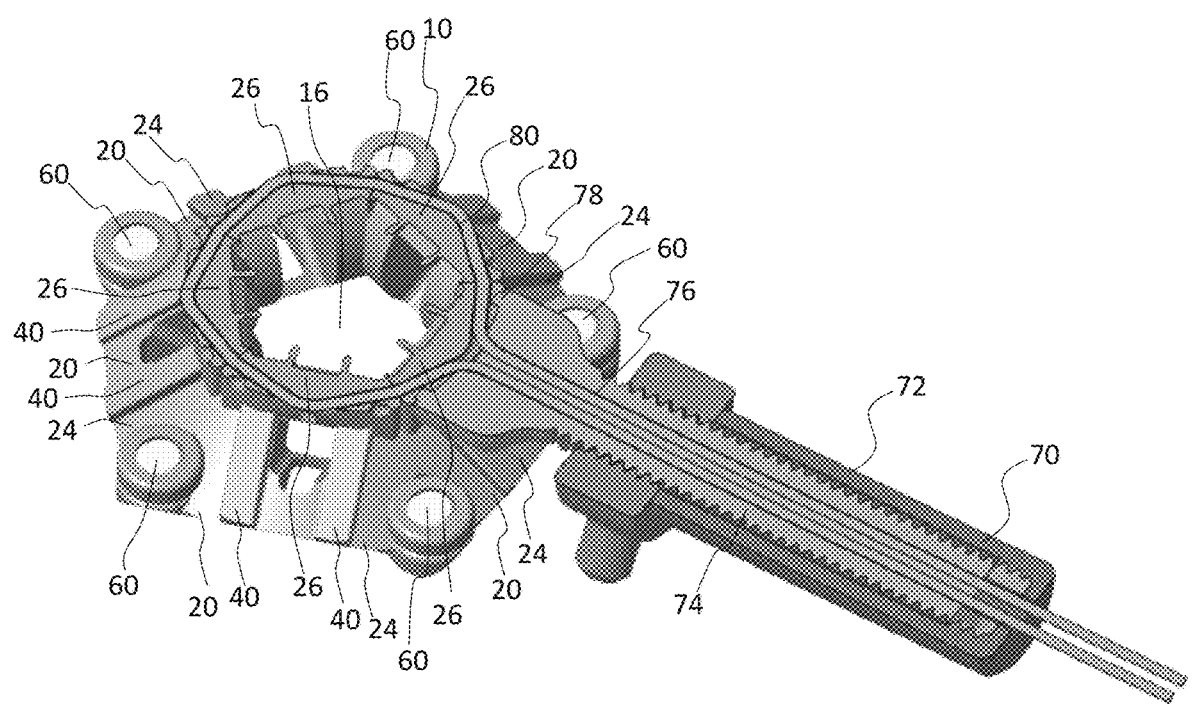
FIG. 14 is a cross-sectional view of the articulating expandable fusion device in an expanded position and the instrument expanding the fusion device.

With further emphasis on FIGS. 13 and 14, the inserter instrument 70 may include guide tube 72, an insertion driver 74 positionable through the guide tube 72, and a wire or cable 76 positionable through the insertion driver 74. As noted with regard to FIGS. 9-12, the guide tube 72 may be configured for deploying the plurality of links 20 into the disc space. The insertion driver 74 and cable 76 may be configured for articulating the plurality of links 20 into a polygon. The cable 76 may be further configured for applying an inward force against the middle bodies 26 of the links 20 to translate the middle bodies 26 towards a center of the polygon to cause linear expansion of the upper and lower bodies 22, 24 of the links 20.

The distal end 78 of the insertion driver 74 may retain the implant 10 to the inserter instrument 70. For example, the distal end 78 of the insertion driver 74 may include one or more engagement features configured for mating with the implant 10. In particular, the distal end 78 of the insertion driver 74 may be configured to mate with one of the middle bodies 26 of one of the links 20. The insertion driver 74 extends through the guide tube 72 and may be threaded to a portion of the guide tube 72 or otherwise engaged thereto.

The wire or cable 76 extends through the insertion driver 74 and is configured to loop 80 around the links 20. In particular, the cable 76 may interface with the middle bodies 26 of the links 20. The cable 76 may extend through one or more openings 51, 53 in the middle bodies 26 of the links 20. In order to articulate the implant 10, a push/pull action may be used. For example, the insertion driver 74 may push the links 20 in the direction D1 while the cable 76 pulls the links 20 in the direction D2, opposite to D1. Although this push/pull articulation is exemplified, it will be appreciated that other articulation methods may be used, such as via one or more cam members, guiding members, or the like.

The wire or cable 76 may loop 80 about the outer perimeter of the links 20. As best seen in FIG. 13, the implant 10 is in the collapsed or contracted position and the cable 76 is looped 80 around and through the middle bodies 26 of the links 20. Turning to FIG. 14, the implant 10 is in the expanded position. To expand the implant 10, the cable 76 may shorten in circumferential distance to provide an inward force that translates the middle bodies 26 inwards toward the center of the polygon. The inward movement of the middle bodies 26 of the links 20 may result in linear expansion of the upper and lower bodies 22, 24 of each of the links 20.

In the collapsed position (FIG. 13), the loop 80 of the cable 76 has a first length and in the expanded position (FIG. 14), the loop 80 of the cable 76 has a second length, shorter than the first length. By applying an inward force against the middle bodies 26 of the links 20, the articulated implant 10 is further expanded such that the distance between the upper and lower endplates 12, 14 is at its greatest height. Although expansion with cable 76 is exemplified herein, it will be appreciated that other mechanisms may be utilized to move the middle bodies 26, such as translation members, linear cams, drive screws, or other suitable devices.

In order to improve the access profile of the interbody implant 10 while maximizing cortical bone contact surface area, methods and systems of installing, articulating, and/or expanding the implant 10 may include one or more of the following. The implant 10 may enter the disc space with a narrow profile and articulate to increase surface area contact on the anterior apophyseal ring. The orientation and position of the interbody implant 10 in its final implanted position may be optimized by pre-/intra-op scans and/or normal population statistics that determine bone mineral density maps of the vertebral body. Robotic and/or navigation guidance may be used to correctly orient the interbody 10. Further details of robotic and/or navigational systems can be found in U.S. Patent Publication No. 2017/0239007, which is incorporated herein by reference in its entirety for all purposes.

In one embodiment, the system may be implanted with one or more of the following steps: (1) A determination is made on final optimal implant location to optimize bone mineral density of the contacted bone/implant interface. (2) Robotic and/or navigation is used to determine the potential trajectories that will allow for this optimal implant location to be achieved. (3) A cannula is docked on the disc space through Kambin's triangle, or the anatomical area that is bordered by the disc space, exiting nerve root, and traversing nerve root. (4) The expandable interbody 10 is inserted in the non-articulated, non-expanded orientation. (5) The expandable interbody 10 is impacted for insertion, and the wire or cable 76 is pulled for articulation. (6) The expandable interbody 10 articulates to a polygonal shape that precisely matches the native disc space anatomy. (7) The expandable interbody 10 expands by shortening the cable 76 about the middle bodies 26 of the links 20 and translating them inwards toward a center of the polygonal shape.

The features of the embodiments described herein may provide one or more of the following advantages. A small insertion profile such as an 8.5 mm lateral insertion profile and minimal insertion height into the disc space may reduce skin, fascia, muscle, and/or ligamentous disruption. The large endplate surface area contact may help to reduce the risk of subsidence, or migration of the implant through the bone endplates of the inferior and superior interbody, especially during expansion. Due to the expansion profile of the implant, reduced endplate disruption may result. The expansion mechanism may reduce the need for traditional trialing of interbody implants which may contribute to endplate disruption. It will be appreciated that different or additional advantages may also be achieved based on the disclosure herein.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An expandable implant comprising:
a first link, a second link pivotally connected to the first link, and a third link pivotally connected to the second link,
each of the links comprises an upper body having one or more ramped surfaces, a lower body having one or more ramped surfaces, and a middle body positioned between the upper and lower bodies and having one or more ramped surfaces, wherein translation of the middle bodies causes the one or more ramped surfaces of the middle bodies to slide against the one or more ramped surfaces of the upper and lower bodies, thereby resulting in expansion of the expandable implant,
wherein the one or more ramped surfaces of the upper and lower bodies, respectively, define male ramps, and the one or more ramped surfaces of the middle bodies define female ramps.

2. The expandable implant of claim 1, wherein the first, second, and third links are configured to articulate into a polygonal shape.

3. The expandable implant of claim 2, wherein the implant further includes a fourth link and a fifth link, wherein the links are configured to articulate into a pentagon.

4. The expandable implant of claim 1, wherein the male ramps of the upper and lower bodies mate with the female ramps of the middle bodies with dovetail slide ramps.

5. The expandable implant of claim 1, wherein the upper body mates with the middle body at a single ramp, and the lower body mates with the middle body at two ramps.

6. The expandable implant of claim 1, wherein each of the upper bodies includes first and second upper retaining rings, and each of the lower bodies includes first and second lower retaining rings, wherein the second upper retaining ring of the first link connects to the first upper retaining ring of the second link with a first pivot pin, the second lower retaining ring of the first link connects to the first lower retaining ring of the second link with a second pivot pin, the second upper retaining ring of the second link connects to the first upper retaining ring of the third link with a third pivot pin, and the second lower retaining ring of the second link connects to the first lower retaining ring of the third link with a fourth pivot pin.

7. An implantable device comprising:
a plurality of links configured to articulate with respect to one another, each of the links comprises an upper body, a lower body, and a middle body positioned between the upper and lower bodies, the upper body includes an upper bone contacting surface configured to engage bone and a lower surface having a first ramp, the lower body includes an upper surface having a second ramp and a lower bone contacting surface configured to engage bone, the middle body includes an upper surface having a third ramp and a lower surface having a fourth ramp, the first ramp of the upper body mates with the third ramp of the middle body and the second ramp of the lower body mates with the fourth ramp of the middle body,
wherein movement of the middle body causes the third ramp to slide against the first ramp and the fourth ramp to slide against the second ramp, thereby resulting in an outward expansion of the upper and lower bodies of the plurality of links
wherein the first and second ramps of the upper and lower bodies, respectively, define male ramps, and the third and fourth ramps of the middle body define female ramps.

8. The implantable device of claim 7, wherein the plurality of links are configured to articulate into a polygonal shape.

9. The implantable device of claim 8, wherein the plurality of links includes five links configured to articulate into a pentagon.

10. The implantable device of claim 7, wherein the male ramps of the upper and lower bodies mate with the female ramps of the middle body with dovetail slide ramps.

11. The implant device of claim 7, wherein the lower body includes a fifth ramp parallel to the second ramp, and the middle body includes a sixth ramp parallel to the fourth ramp, wherein the fifth ramp of the lower body mates with the sixth ramp of the middle body.

12. The implantable device of claim 7, wherein the plurality of links connect at a plurality of joints.

13. The implantable device of claim 12, wherein the plurality of joints comprise retaining rings and pivot pins.

14. The implantable device of claim 13, wherein the upper body includes first and second upper retaining rings, and the lower body includes first and second lower retaining rings, the first retaining ring of the upper body is aligned with the first retaining ring of the lower body, and the second retaining ring of the upper body is aligned with the second retaining ring of the lower body.

15. An implantable system comprising:
an articulatable and expandable implant, the implant comprises a plurality of links pivotally connected to one another, each of the links comprises an upper body having one or more ramped surfaces, a lower body having one or more ramped surfaces, and a middle body positioned between the upper and lower bodies and having one or more ramped surfaces configured to mate with the one or more ramped surfaces of the upper and lower bodies, respectively, and
an inserter instrument having a guide tube, an insertion driver, and a cable, the guide tube is configured for deploying the plurality of links into a disc space, the insertion driver and cable are configured for articulating the plurality of links into a polygon, and the cable is further configured for applying an inward force against the middle bodies of the links to translate the middle bodies towards a center of the polygon, thereby causing linear expansion of the upper and lower bodies.

16. The implantable system of claim 15, wherein the middle body includes a plurality of openings configured for receiving the cable therein.

17. The implantable system of claim 15, wherein the cable is configured to shorten in circumferential distance to provide the inward force against the middle bodies and translate the middle bodies inwards toward the center of the polygon.

18. The implantable system of claim 15, wherein the insertion driver applies a push force to the plurality of links and the cable applies a pull force to the plurality of links to articulate the plurality of links.

* * * * *